United States Patent [19]

Nakanishi

[11] 4,353,697
[45] Oct. 12, 1982

[54] DENTAL HANDPIECE AND A CONNECTING MEANS THEREOF

[75] Inventor: Takasuke Nakanishi, Kanuma, Japan

[73] Assignee: Nakanishi Dental Manufacturing Co., Kanuma, Japan

[21] Appl. No.: 169,320

[22] Filed: Jul. 16, 1980

[30] Foreign Application Priority Data

Jan. 21, 1980 [JP] Japan ............................. 55-6320[U]

[51] Int. Cl.$^3$ .............................................. A61C 1/08
[52] U.S. Cl. .................................................... 433/126
[58] Field of Search ..................... 433/80, 89, 84, 82, 433/85, 126

[56] References Cited

U.S. PATENT DOCUMENTS 3,936,940  2/1976  Loge .................................... 433/126
4,217,101  8/1980  Loge .................................... 433/126

Primary Examiner—Robert Peshock
Attorney, Agent, or Firm—Armstrong, Nikaido, Marmelstein & Kubovcik

[57] ABSTRACT

An air-powered dental handpiece and a connecting means comprises a handle portion and a powerhead assembly. A sleeve bearing having a forwardly reducing cylindrical internal surface is integrally held into another end opening of the handle portion. The surface has three stepped annular space walls, and a central air supply passage and two axial passages for exhaust and water are provided to extend to the stepped annular space walls. An air supply pipe is fixedly inserted into the central passage and two pipes are fixedly inserted into two passages. A front portion of a connecting means is so formed into a forwardly reducing cylindrical plug as to fit into a socket of the sleeve bearing. The plug is provided with a top flat wall and two stepped annular space walls to form a neck journal, which is journaled in the sleeve bearing, thus bringing the top flat wall of the plug in close proximity to the innermost stepped wall of the sleeve bearing and two stepped annular walls of the plug in close proximity to the two stepped annular walls of the bearing respectively and communicating the passages of the plug with those of the bearing. A push-pull rod having a head at its outer end and a right angle hook at its inner end is put into a cylindrical casing of the plug by a dead spring, thus enabling a dentist to easily remove or reinsert a handle portion from or into the connecting means and also assuring smooth operation.

3 Claims, 10 Drawing Figures

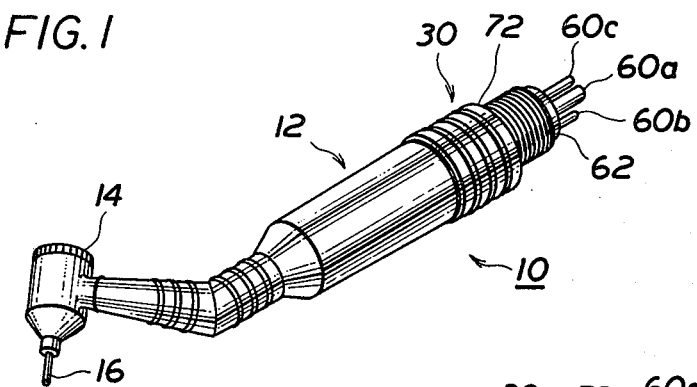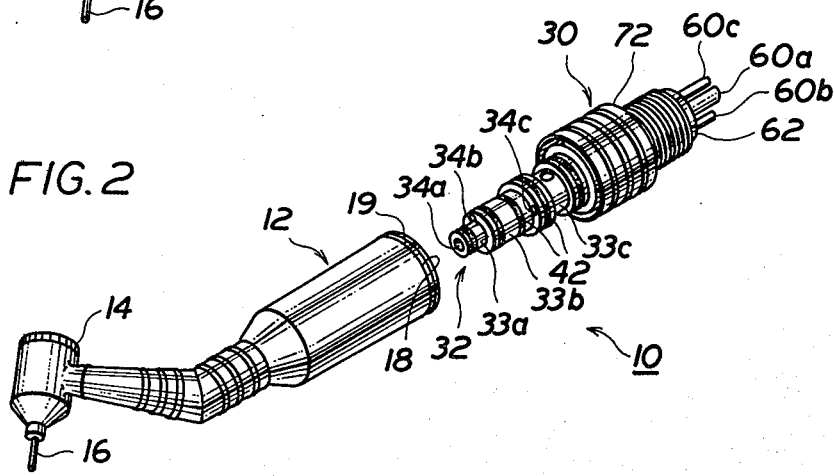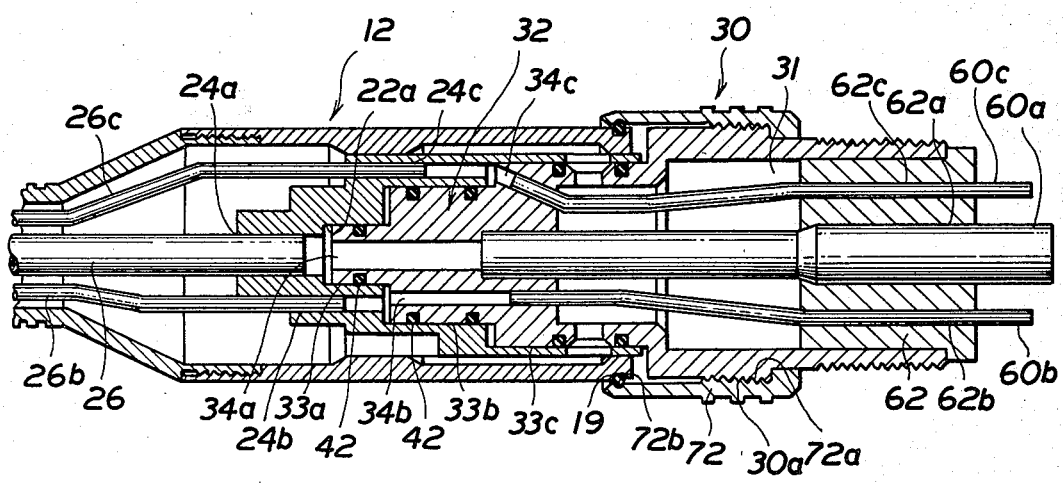

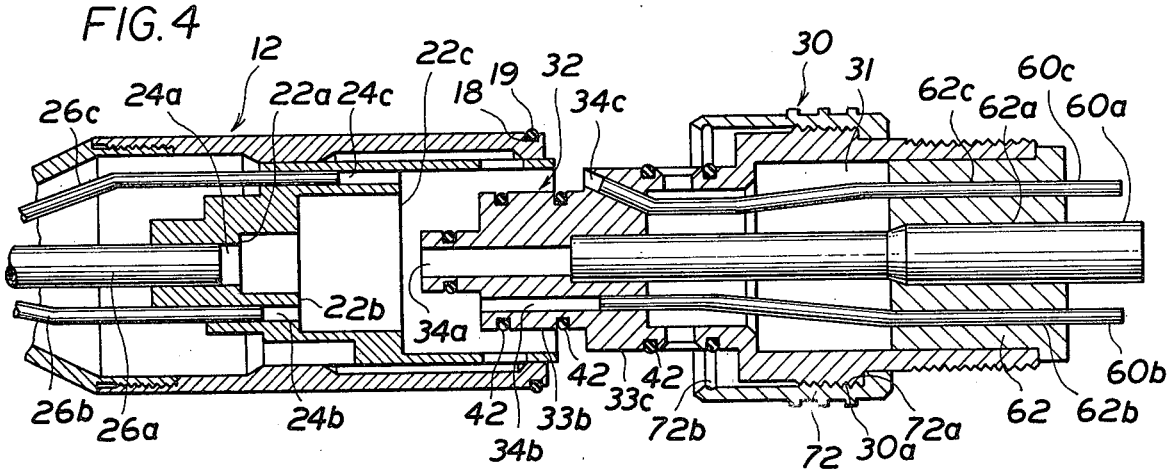
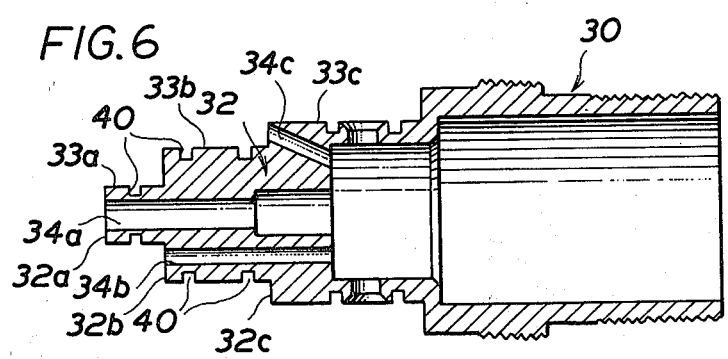
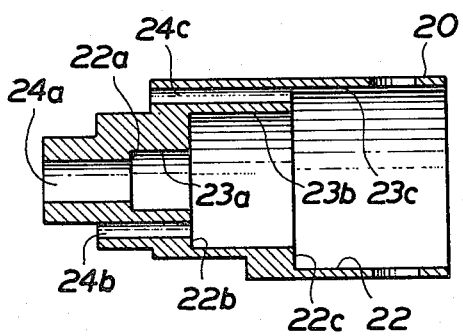
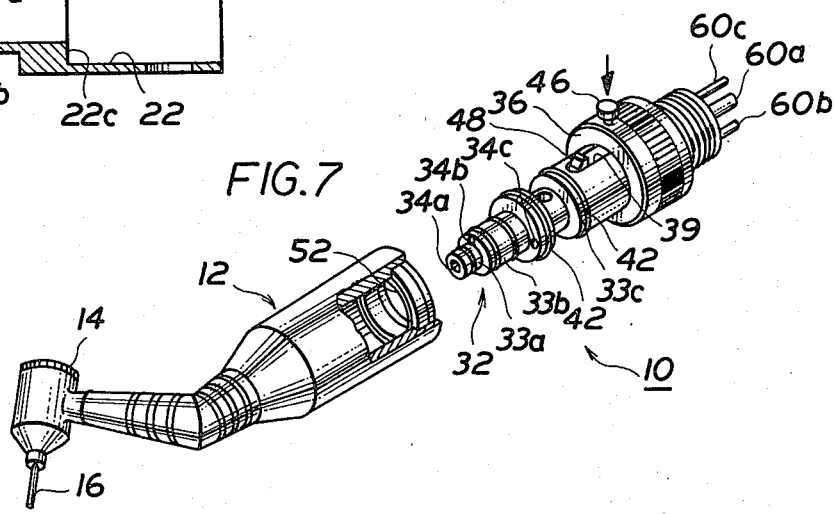

DENTAL HANDPIECE AND A CONNECTING MEANS THEREOF

BRIEF SUMMARY OF THE INVENTION

This invention relates to improvements in a dental handpiece and a connecting means thereof which enables a dentist to easily remove or reinsert a handle portion from or into the connecting means and also assuring smooth operation of the dental handpiece.

A handle portion of the dental handpiece including a head and an air-powered turbine wheel for driving a tool carrying spindle is often removed from a connecting means either for sterilization, exchanging worn out parts, repairs, cleaning or for inspection. The removal and reinsertion of the handle portion should be done easily and rapidly. Dental tools such as drills, buffers, reamers, or the like are driven to rotate by an air-powered turbine so that a handle portion thereof must be secured into a connecting means tightly, but allowing circumferential slidable rotation between the handle portion and the connecting means.

The conventional dental handpiece is complicated in construction and requires troublesome operation for removal and reinsertion of the handle portion.

A principal object of this invention is to provide a dental handpiece and a connecting means thereof whereby a handle portion of the dental handpiece can be either removed from a connecting means as a unit assembly or jointed into the connecting means quite easily and quickly.

Another object of this invention is to provide a dental handpiece whereby any leakage such as air or water can be completely prevented.

Another object of this invention is to provide a dental handpiece which can be driven smoothly and quietly.

Still another object of this invention is to provide a dental handpiece which is comparatively simple and small in construction, light in weight and at the same time desirably rigid, strong and durable.

BRIEF DESCRIPTION OF DRAWINGS

While I have shown in the accompanying drawings, a preferred embodiment of my invention, it should be understood that the same is susceptible of modification and change without departing from the spirit of my invention.

FIG. 1 is a perspective view of the first embodiment of the dental handpiece, as contemplated in a preferred embodiment of the invention;

FIG. 2 is a perspective view of the dental handpiece shown in FIG. 1, disassembled into a handle portion and a connecting means;

FIG. 3 is an enlarged vertical longitudinal sectional view of the dental handpiece shown in FIG. 1;

FIG. 4 is an enlarged vertical longitudinal sectional view, illustrating a connecting means being disassembled out of a handle portion;

FIG. 5 is an enlarged vertical sectional view of a sleeve bearing to be integrally held into a handle portion;

FIG. 6 is an enlarged vertical sectional view of a connecting means to be rotatably journaled in a sleeve bearing;

FIG. 7 is an exploded perspective view of the second embodiment of the dental handpiece, partly cut out of a handle portion;

DETAILED DESCRIPTION OF THE INVENTION

Figure 8:
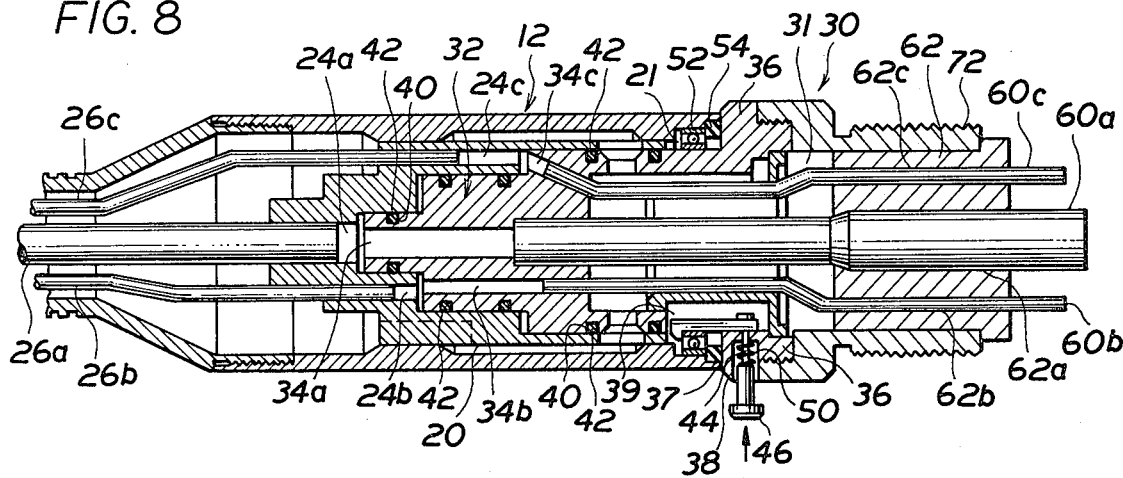
FIG. 8 is an enlarged vertical longitudinal sectional view of the dental handpiece shown in FIG. 7.

Referring to the drawings, the dental handpiece 10 of the present invention comprises a handle portion 12 and a powerhead assembly 14 which is supported on a top end of the handle portion. At the end of the powerhead assembly 14 is a pneumatic motor (not shown) which operates, when energized, to rotate at high speed a dental burr or reamer shown at 16.

An inwardly recessed slot 18 is provided around a circumferential surface of the handle portion 12 near a rear end thereof. An annular spring 19 is fitted into the slot 18.

As shown in FIGS. 4-6, a sleeve bearing 20 having a forwardly reducing cylindrical internal surface 22 is integrally held into another end opening of the handle portion 12. As particularly shown in FIG. 5, the forwardly reducing cylindrical surface 22 includes three stepped annular space walls 22a, 22b and 22c which are adjacent and perpendicular to circumferential internal regions 23a, 23b and 23c respectively. A central air supply passage 24a and two passages 24b and 24c for exhaust and water are axially provided to extend through a substantial length of the sleeve bearing 20.

An end of a pipe 26a supplying air under pressure is fixedly inserted into the passage 24a, an end of a pipe 26b for exhaust is firmly put into the passage 24b and an end of a pipe 26c for water is fixedly joined into the passage 24c respectively. A rear internal portion of the sleeve bearing 20 is so shaped as to form a socket 28 for snugly receiving a connecting means 30.

A front portion of the connecting means 30 is so formed into a forwardly reducing cylindrical plug 32 like a neck journal as to fit into the socket 28 of the sleeve bearing 20.

The plug 32 is a forwardly reducing cylinder having a top flat wall 32a and two stepped annular space walls 32b and 32c to form a neck journal. A central air supply passage 34a and an exhaust passages 34b are axially provided to extend through a solid portion of the plug 32 of the connecting means 30. A forwardly outwardly biased passage 34c for water is provided from the socket 28 to the annular space wall 32c. When the plug 32 of the connecting means 30 is inserted into the sleeve bearing 20, the top flat wall 32a is brought in close proximity to the stepped annular wall 22a of the sleeve bearing 20, the stepped annular wall 32b to the stepped annular wall 22b and the stepped annular wall 32c to the stepped annular wall 22c respectively.

A top end of a pipe 60a supply air under pressure is inserted into the passage 34a, a top end of an exhaust pipe 60b for air, water and tooth chip is put into the passage 34b and also a top end of a pipe 60c supplying water is inserted into the passage 34c respectively. A cylindrical hollow chamber 31 is shaped within a substantial length of the connecting means 30.

Recessed inwardly from the cylindrical wall of the plug 32, at circumferentially distributed points, are slots 40, into each of which a seal ring 42 is fitted respectively.

A hollow mount insert 62 having three axial openings 62a, 62b and 62c is secured into a rear end interior of the connecting means 30, through which pipes 60a, 60b and 60c are penetrated to extend out of the insert 62.

Securing the connecting means 30 into the sleeve bearing 20 within the handle portion 12 is a mounting nut 72 with internal threads 72a and screwed onto external threads 30a on the connecting means 30.

It should be obvious to those skilled in the art that on turning of the nut 72 whereby it is advanced axially onto the connecting means 30, such serves to bring it toward the handle portion 12 and also to fit the annular spring 19 into the annular slot 72b of the nut 72. In this way, the connecting means 30 and the handle portion 12 are mounted together to form the dental handpiece 10.

Accordingly, the plug 32 of the connecting means 30 is rotatably fitted and snugly received in position in the socket 28 of the sleeve bearing 20 so that the top flat wall 32a of the plug is brought in close proximity to the stepped annular wall 22a of the sleeve bearing to communicate the pipe 26a with the pipe 36a, the stepped annular wall 32b is brought in close proximity to the stepped annular wall 22b to connect the pipe 26b with the pipe 46b, and the stepped annular wall 32c is brought in close proximity to the stepped annular wall 22c to connect the pipe 26c with the pipe 36c respectively. Thus, the plug 32 of the connecting means 30 is tightly secured into the sleeve bearing 20, allowing circumferential slidable rotation between the plug and the sleeve bearing.

Figure 9:
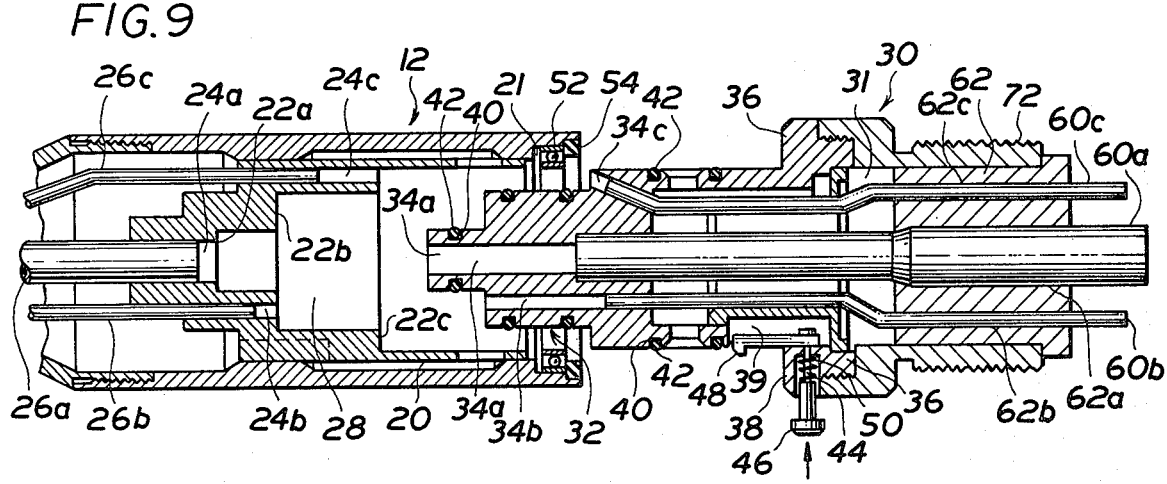
FIG. 9 is an enlarged vertical longitudinal sectional view, illustrating a connecting means being disassembled out of a handle portion.
Figure 10:
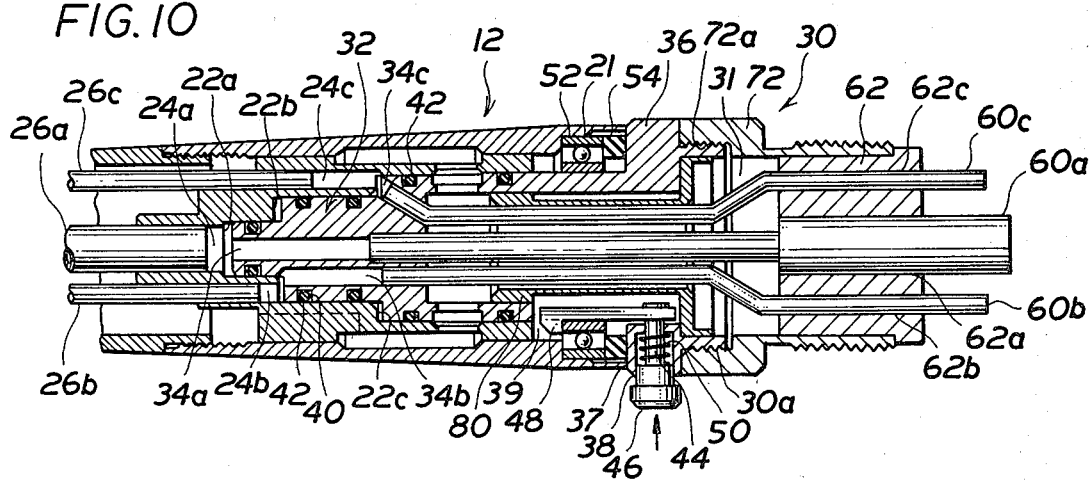
FIG. 10 is a sectional view, on a somewhat enlarged scale, of the dental handpiece shown in FIGS. 7-9, illustrating the internal portions including a handle portion, a sleeve bearing, passages, pipes, a locking device and a plug of a connecting means.

In FIGS. 7-10, a bearing retainer 52 including a plurality of roller bearings therein is fitted into an inlet peripheral recess 21 of the handle portion 12, which retainer being held in position by a journal packing 54.

A peripheral flange 36 of the connecting means 30 is brought in close proximity to the end wall 13 of the handle portion 12 and also with the journal packing 54 when the plug 32 of the connecting means is inserted into the socket 28 of the sleeve bearing 20. A radial socket 37 is provided through the peripheral flange 36 to extend into an axial groove 39 provided through a wall of the plug 32. A cylindrical casing 38 is fixedly put into the radial socket 37. A push-pull rod 44 having a head 46 at its outer end and a right angle hook 48 at its inner end is put into the casing 38 by means of a dead spring 50 to constitute a locking device so that the hook 48 is introduced into the axial groove 39, thus always urging the rod 44 outwardly by the dead spring 50.

For securing, the plug 32 is introduced into the socket 28 of the sleeve bearing 20 while pushing down with a finger tip the head 46 of the push-pull rod 44 inwardly into the hollow chamber 31 until the top flat wall 32a is brought in close proximity to the innermost stepped annular wall 22a. When the finger is taken off in position, the push-pull rod 44 is protruded outwardly by resiliency of the dead spring 50 to engage the hook 48 with a front annular wall of the bearing retainer 52. Unless the head 46 of the rod 44 is pushed again inwardly, the plug 32 does not separate out of the sleeve bearing 20. In this way, the plug 32 is mounted into the sleeve bearing 20 so as to constitute the dental handpiece 10.

While an embodiment of the invention has been described, it is obvious that variations and modifications are possible without departing from the invention. It is desired to cover all such forms of the invention as would be apparent to one skilled in the art, and that come within the scope of the appended claims.

I claim:

1. A dental handpiece comprising: a handle portion and a powerhead assembly which is supported on a top end of said handle portion; a sleeve bearing tightly held into a rear end opening of said handle portion, said sleeve bearing having a fowardly reducing cylindrical internal surface, said cylindrical internal surface including three stepped annular space walls adjacent and perpendicular to circumferential internal regions respectively; a central air supply passage and two passages for exhaust and water axially provided to extend through a substantial length of said sleeve bearing; an air supply pipe inserted into said central air supply passage and two pipes for exhaust and water inserted respectively into two axial passages, a rear internal portion of said sleeve bearing being so shaped as to form a socket for snugly receiving a plug of connecting means; a connecting means to be inserted into said sleeve bearing, a front portion of said connecting means being so formed into a forwardly reducing cylindrical plug as to fit into said socket of said sleeve bearing, said plug including a central axial straight passage for an air pipe and another straight passage for an exhaust pipe and a forwardly outwardly biased water passage provided from the socket to a rearmost annular space wall, said plug including a plurality of inwardly recessed slots at circumferentially distributed points, each slot including a seal; an air supply pipe inserted into said axial air passage; an exhaust pipe inserted into another axial passage; a water pipe inserted into said forwardly outwardly biased passage; a hollow mount insert having three axial openings and secured into a rear end interior of said connecting means for allowing said three pipes to penetrate therethrough; a mounting nut provided with internal threads and screwed onto external threads on said connecting means; a bearing retainer including a plurality of roller bearings therein and fitted into an inlet peripheral recess of said handle portion; a radial socket provided through a peripheral flange to extend into an axial groove provided through a wall of said plug; a cylindrical casing fixedly set in said radial socket; and a push-pull rod having a head at its outer end and a right angle hook at its inner end held in said casing by a dead spring, whereby the introduction of said hook into said axial groove engaging a front annular wall of said bearing retainer and constant urging of said rod outwardly by said dead spring forms a locking device.

2. A dental handpiece as set forth in claim 1 wherein said plug of the connecting means is snugly inserted into said sleeve bearing to allow circumferential slidable rotation between said plug and said sleeve bearing.

3. A dental handpiece as set forth in any one of claims 1 or 2 wherein with an insertion of said plug into said sleeve bearing, a top flat wall of said plug is brought in close proximity to said innermost stepped annular wall of said sleeve bearing, and two stepped annular walls of the plug are brought in close proximity to the stepped annular walls of said sleeve bearing.

* * * * *